United States Patent [19]

Smith

[11] Patent Number: 4,648,841
[45] Date of Patent: Mar. 10, 1987

[54] UPPER DENTURE ATTACHMENT MEANS

[76] Inventor: Kenneth J. Smith, 234 Medical Cir., Morehead, Ky. 40351

[21] Appl. No.: 824,673

[22] Filed: Jan. 31, 1986

[51] Int. Cl.⁴ ............................................... A61C 8/00
[52] U.S. Cl. ..................................................... 433/173
[58] Field of Search ......................... 433/173, 215, 225

[56] References Cited

U.S. PATENT DOCUMENTS 3,919,772 11/1975 Lenczycki ............................ 433/173
4,370,134 1/1983 Roberts ................................ 433/173
4,516,937 5/1985 Bosker ................................. 433/173

*Primary Examiner*—Robert Peshock
*Attorney, Agent, or Firm*—Edward M. Steutermann

[57] ABSTRACT

A procedure for the permanent attachment of upper dentures to the maxilla of the human mouth including sliting the maxilla horizontally immediately above the nasal floor, with the maxilla in a down fractured position, drilling at least one hole through the severed portion of the maxilla in a direction lateral to the slit, inserting a generally planar retaining device cooperative fastener means located therein where the fastener means are located over the hole to provide access from the bottom side of the maxilla, returning the maxilla to approximately its original position, with the retaining device located in the slit and fastening the severed portion of the maxilla to the balance of the maxilla to allow healing thereof with the retainer in place.

1 Claim, 6 Drawing Figures

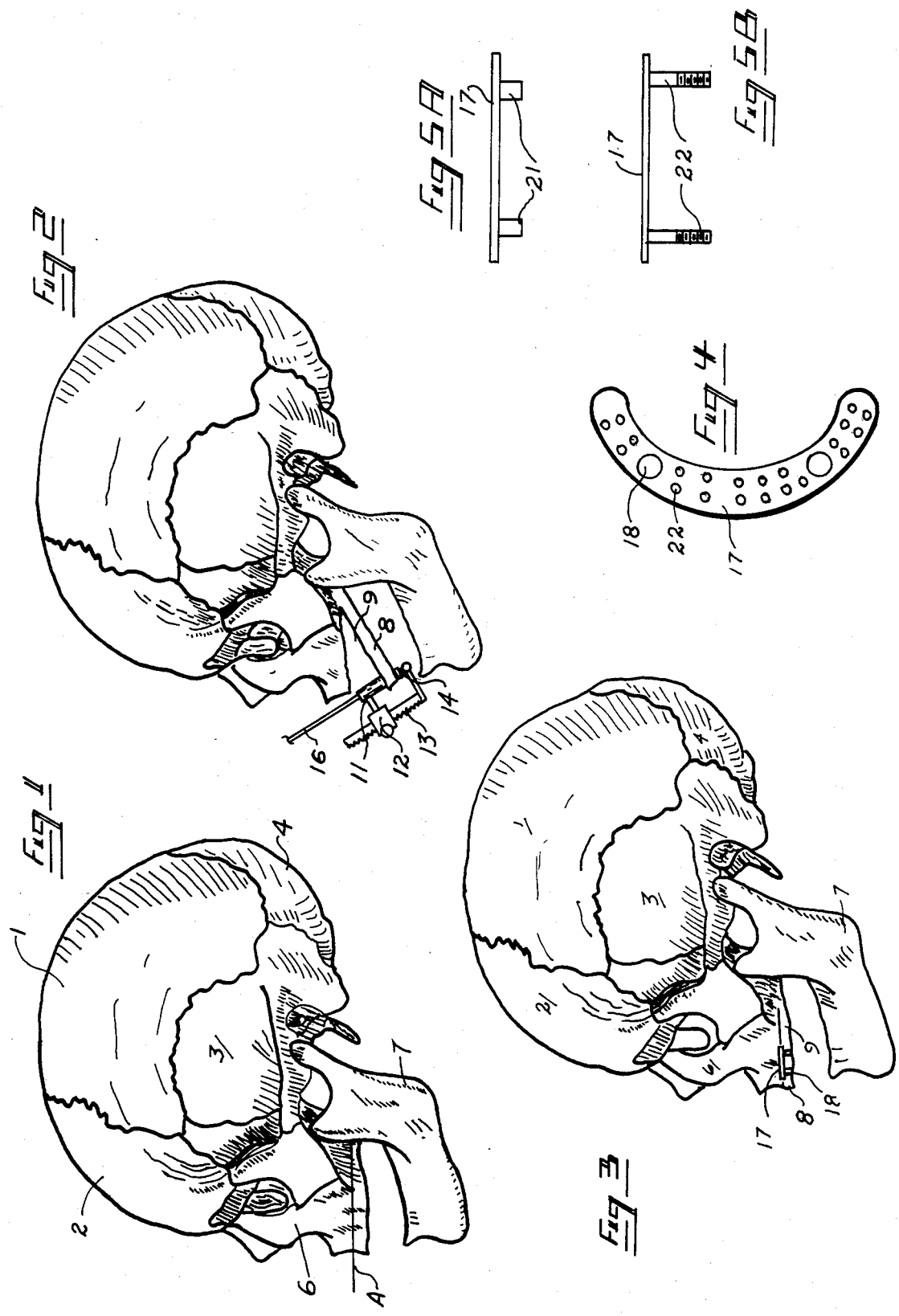

UPPER DENTURE ATTACHMENT MEANS

SUMMARY OF THE INVENTION

The present invention relates to dental procedures, and primarily to a dental procedure providing a permanent fastening means located in the maxilla for securing upper dentures in the human mouth.

Various prior art arrangements are known for attachment means for securing dentures to the mandibular or lower jaw bone. One procedure is shown in U.S. Pat. No. 664,022 where a mandibular staple bone plate is provided have protrusions or fasteners utilized to secure a set of dentures to the lower jaw.

The procedure taught in the prior art reference for attachment of a fastening device to the mandibular is substantially different from the present procedure inasmuch as the sinsus of the skull intervene and prevent use of the procedure thought by the reference patent.

While other procedures are known to permit fastening dentures to the maxilla, in a permanent or semi permanent fashion such procedures are generally complex, in many cases require hospitalization and for many patients are prohibitively expensive.

No prior art arrangement is known which teaches a procedure which allows the permanent attachment of a fastener device within the maxilla where the pin includes fastener means to which a set of dentures can be secured.

BACKGROUND OF THE INVENTION

As previously stated, the present invention relates to a new, useful and straight foward procedure for the installation of a fastener device in the maxilla to allow the attachment of a set of upper dentures in a human being.

Procedures currently available, are extremely expensive, complicated, present some dangers and generally are performed in hospital inpatient basis. On the contrary, procedures within the scope of the present invention are inexpensive, can be done without hospitalization, and are for less time consuming then the prior art procedures.

Procedures within the scope of the present invention can be done on an outpatient basis or in a dental office or clinic where desired.

More particularly, the present invention provides a procedure for the permanent attachment of upper dentures to the maxilla of the human mouth including slitting the maxilla horizontally immediately above the nasal floor, with the maxilla in a down fractured position, drilling at least one hole through the severed portion of the maxilla in a direction lateral to the slit, inserting a generally planar retaining device cooperative fastener means located therein where the fastener means are located over the hole to provide access from the bottom side of the maxilla, returning the maxilla to approximately its original position, with the retaining device located in the slit and fastening the severed portion of the maxilla to the balance of the maxillato allow healing thereof with the retainer in place.

While various alternative procedures within the scope of the present invention will occur to those skilled in the art upon reading the disclosure set forth hereinafter. One procedure in accordance with the present invention and the associated material, is illustrated in the accompanying figures which are by way of illustration only but not by way of limitation.

BRIEF DESCRIPTION OF THE DRAWINGS

In the example in accordance with the present invention shown in the accompanying drawings and discussed hereinafter:

FIG. 1 is an elevational view of a normal skull without dentures;

FIG. 2 is an illustration of a skull where the maxilla has been slit in accordance with the present invention and illustrating one drilling procedure within the scope of the present invention;

FIG. 3 is an illustration of the skull of FIGS. 1 and 2 with the split portion of the maxilla replaced;

FIG. 4 is a plan view of an example of a fastener device in accordance with the present invention; and FIGS. 5A and 5B illustrate elevational views of examples of devices within the scope of the present invention.

DETAILED DESCRIPTION OF THE DRAWINGS

Referring first to FIGS. 1-3, a skull including the frontal lobe 2, parietal lobe 1, the occipital 4, the maxilla 6 and the mandible 7, are shown as previously discussed, the purpose of the invention is to facilitate the installation of dentures on the lower side of the maxilla.

The initial portion of the operation includes splitting the maxilla 6 along the line A thereby making a horizontal break of the maxilla above the nasal floor.

The maxilla is then separated along the split to form an opening 9, as shown in FIG. 2, where the lower portion of the maxilla is separated.

Holes are then drilled in the separated portion 8 of the maxilla where a is used having a rack 13, is provided with a gear assembly 12 which holds the guide 11, as is known in the art, so the device can be clamped to the separated portion of the maxilla between foot 14 and the guide 11. A drill bit 16 is utilized to be guided by guide 16 to selectively drill holes in the separated portion 8 of the maxilla at selected spacing to allow insertion of a plate 17, an example of which is shown in FIG. 4 to secure a denture.

Referring to FIG. 4, the plate 17 is shaped to conform generally to the shape of the edge of the maxilla and is of a width sufficient so that when in place the maxilla will grow around the outer edges of the plate.

Fastening means 18, examples of which are described hereinafter, are carried by the plate 17 and the holes which have been drilled by the drill bit 16, as previously described, are selectively positioned to receive the fastening devices 18.

FIGS. 5A and 5B illustrate examples of the fastening devices 18, which can be utilized, but it will be understood the examples shown in FIGS. 5A and 5B are not by way of limitation but by way of example only, it being also understood that in certain applications other type fastening devices can also be used.

In FIG. 5A fastening devices 18 include bosses 21, as is known in the art, which are drilled and tapped in order to receive cooperative threaded shafts. In these examples the plate 17 would be placed in the maxilla so that threaded shafts can be placed through the dentures (not shown) which are subsequently placed on the lower edge of the separated portion 8 of the maxilla and held in place by being received in the bosses 21.

Alternatively, as shown in FIG. 5B, threaded studs 22 can be provided to extend through the cooperative holes drilled in the separated portion 8 of the maxilla so that the threaded portions extend through the separated portion 8 and the dentures are then placed on the threaded shafts and secured thereto by cooperative nuts (not shown).

As also shown in FIG. 4, plate 17 can include holes 22 extending substantially through the plate, which have been found to allow the maxilla to grow through the holes and provides further support through the plate upon healing.

Additionally in accordance with the present invention, plate 17 is placed on top of the separated portion 8 of the maxilla with the fasteners 18 extending therethrough. As shown in FIG. 3 the lower portion of the maxilla is then replaced in contiguous relation with the maxilla and wired or fastened by other means to allow healing and repair.

Subsequently dentures (not shown) can be affixed to the fasteners 18 and are permanently or semi permanently located in place.

It will be understood that the foregoing is but one procedure within the scope of the present invention and that other procedures also within the scope of the present invention will occur to those skilled in the art upon reading the disclosure setforth hereinbefore.

The invention claimed is:

1. A procedure for the permanent attachment of upper dentures to the maxilla of the human mouth including sliting the maxilla horizontally immediately above the nasal floor, with the maxilla in a down fractured position, including drilling at least one hole through the severed portion of the maxilla in a direction lateral to the slit, inserting a generally planar retaining device with cooperative fastener means located therein where the fastener means are located over the said to provide access from the bottom side of the maxilla, returning the maxilla to approximately its original position with the retaining device located in the slit and fastening the severed portion of the maxilla to the balance of the maxillato allow healing thereof with the retainer in place.

* * * * *